(12) United States Patent
Grunewald

(10) Patent No.: US 9,174,023 B2
(45) Date of Patent: Nov. 3, 2015

(54) UNIDIRECTIONAL CATHETER CONTROL HANDLE WITH TENSIONING CONTROL

(71) Applicant: Biosense Webster (Israel), Ltd., Yokneam (IL)

(72) Inventor: Debby Grunewald, Los Angeles, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 19 days.

(21) Appl. No.: 13/736,020

(22) Filed: Jan. 7, 2013

(65) Prior Publication Data

US 2014/0194813 A1 Jul. 10, 2014

(51) Int. Cl.
*A61M 25/01* (2006.01)
*A61B 18/14* (2006.01)
*A61B 18/00* (2006.01)
*A61B 19/00* (2006.01)

(52) U.S. Cl.
CPC ............ *A61M 25/0147* (2013.01); *A61B 18/14* (2013.01); *A61M 25/0136* (2013.01); *A61B 18/1492* (2013.01); *A61B 2018/00351* (2013.01); *A61B 2019/5251* (2013.01); *A61B 2218/002* (2013.01)

(58) Field of Classification Search
CPC .................. A61M 25/0147; A61M 2025/0175; A61M 2025/0004; A61B 2017/003
USPC .................................. 600/131; 604/95.04, 528
See application file for complete search history.

(56) References Cited

U.S. PATENT DOCUMENTS

| | | | | |
|---|---|---|---|---|
| 5,195,968 A | * | 3/1993 | Lundquist et al. | 604/95.04 |
| 5,383,923 A | * | 1/1995 | Webster, Jr. | 607/125 |
| 5,465,716 A | * | 11/1995 | Avitall | 600/374 |
| 5,480,382 A | | 1/1996 | Hammerslag et al. | |
| 5,603,697 A | * | 2/1997 | Grundy et al. | 604/95.04 |
| 5,964,757 A | * | 10/1999 | Ponzi | 606/45 |
| 6,123,699 A | * | 9/2000 | Webster, Jr. | 604/528 |
| 6,183,463 B1 | * | 2/2001 | Webster, Jr. | 604/528 |
| 6,394,976 B1 | * | 5/2002 | Winston et al. | 604/95.04 |

(Continued)

FOREIGN PATENT DOCUMENTS

| | | |
|---|---|---|
| EP | 1 033 144 A1 | 9/2000 |
| EP | 1 245 245 A2 | 10/2002 |

(Continued)

OTHER PUBLICATIONS

EP Communication dated Apr. 7, 2014 and Extended European Search Report for European Application No. EP 14150228, 8 pgs.

(Continued)

*Primary Examiner* — Gerald Landry, II
(74) *Attorney, Agent, or Firm* — Christie, Parker & Hale, LLP

(57) ABSTRACT

A catheter includes a tip electrode with a shell and a support member to provide a plenum chamber. The plug is formed with a U-shaped passage for a safety line to wrap around and secure the support member (with the shell affixed thereto) to the catheter. Additional passages are formed in the plug to accommodate components such as irrigation tubing, lead wire and thermocouple wire pair. A method of manufacture provides distal installation and/or anchoring of the safety line, lead wire and thermocouple wire pair in the support member prior to sealing the support member and mounting the shell.

15 Claims, 6 Drawing Sheets

(56) References Cited

U.S. PATENT DOCUMENTS

| | | | |
|---|---|---|---|
| 6,468,260 B1* | 10/2002 | Bumbalough et al. | 604/523 |
| 6,976,955 B2* | 12/2005 | Hardin et al. | 600/131 |
| 7,081,106 B1 | 7/2006 | Guo et al. | |
| 8,079,982 B1* | 12/2011 | Ponzi et al. | 604/115 |
| 2007/0157162 A1* | 7/2007 | Ciolfi | 717/105 |
| 2007/0191865 A1* | 8/2007 | Pappas | 606/108 |
| 2007/0239105 A1* | 10/2007 | Weitzner et al. | 604/95.01 |
| 2011/0251554 A1 | 10/2011 | Romoscanu | |
| 2012/0215097 A1* | 8/2012 | Ponzi et al. | 600/431 |
| 2012/0277755 A1* | 11/2012 | Liu et al. | 606/94 |
| 2012/0323175 A1* | 12/2012 | Vogelbaum et al. | 604/95.04 |

FOREIGN PATENT DOCUMENTS

| | | |
|---|---|---|
| EP | 1 690 564 A1 | 8/2006 |
| EP | 2 165 730 A1 | 3/2010 |
| EP | 2 172 240 A1 | 4/2010 |
| EP | 2 172 241 A2 | 4/2010 |
| WO | WO 01/78825 A2 | 10/2001 |
| WO | WO 2006/135774 A1 | 12/2006 |
| WO | WO 2010/035599 A1 | 4/2010 |

OTHER PUBLICATIONS

EP Communication dated Apr. 14, 2014 and Extended European Search Report for European Application No. EP 14153915, 9 pgs.

* cited by examiner

UNIDIRECTIONAL CATHETER CONTROL HANDLE WITH TENSIONING CONTROL

FIELD OF INVENTION

The present invention relates to catheters, particular catheters with a deflectable portion and a control handle to control deflection.

BACKGROUND OF INVENTION

Electrode catheters have been in common use in medical practice for many years. They are used to stimulate and map electrical activity in the heart and to ablate sites of aberrant electrical activity. In use, the electrode catheter is inserted into a major vein or artery, e.g., femoral artery, and then guided into the chamber of the heart of concern. Within the heart, the ability to control the exact position and orientation of the catheter tip is critical and largely determines how useful the catheter is.

A typical mapping or ablation catheter has an elongated catheter body, an intermediate deflectable section, a distal section carrying one or more electrodes, and a control handle in which the proximal end of at least one puller wire is anchored. The puller wire extends distally through the catheter body and at least through the intermediate deflectable section. A distal end of the puller wire is typically anchored at or near a junction of the deflectable section and the distal section. A compression coil surrounding the puller wire is generally provided through the catheter body, where a distal end of the compression coil defines an initiation location of the desired deflection. A protective tubing around the puller wire generally provided distal of the compression coil to protect the outer tubing of the catheter from being cut by the puller wire during deflection.

Unidirectional catheters use a single puller wire. Control handles for unidirectional catheter include control handles using a piston that is housed in a handle housing and longitudinally movable relative thereto for actuating the puller wire in achieving a desired deflection. Because the patient's heart is active with blood flow and moving walls and chambers, the catheter is subjected to forces that may cause the catheter to change or lose the deflection without an operator's constant attention and manipulation. Thus, the piston may have a friction-inducing member, for example, an O-ring, situated between the piston and the handle housing to maintain a desired deflection and prevent the piston from sliding or moving under these forces. However, the O-ring may not consistently provide sufficient friction to hold the piston and maintain the desired deflection.

Accordingly, it is desirable to provide a unidirectional catheter control handle with a tension mechanism that can releasably lock the piston in a particular position, and allow repositioning of the piston to a different position and adjusting of the amount of force needed to reposition the piston. Moreover, it is desirable that the mechanism allow control of the tension of deflection for providing a user with an enhanced ability to accurately position the catheter.

SUMMARY OF THE INVENTION

The present invention is directed to a unidirectional catheter with an improved control handle having a tension adjustment assembly enabling the catheter to be releasably locked in a desired deflection and allowing adjustment of the catheter's resistance to deflection.

In one embodiment, the catheter includes a flexible tubing, and a control handle having a housing and a piston in a telescopic configuration, where the piston has a thumb control and the piston is longitudinally slidable relative to the housing by a user via the thumb control for deflecting the tubing. Advantageously, the control handle includes a tension adjustment assembly that provides a force member adapted for applying a force on the piston, and a knob rotationally coupled to the force member, where the knob is adapted for rotation by the user to adjust the force applied on the piston by the force member. The force includes contact, pressure and/or friction between the piston and the housing of the control handle and allows the piston to be releasably locked in a desired position relative to the housing, repositioned relative to the housing and adjustment of the ease by which the piston can be moved relative to the housing. The tension adjustment assembly may also include a guide which limits the range of motion of the knob so as to prevent damage to the piston and/or housing, or disassembly or detachment of the tension adjustment assembly.

In a more detailed embodiment, the force member includes a set screw which extends through an axial bore formed in the knob, where a distal end of the set screw extends through a threaded bore formed in the housing so that the distal end makes adjustable contact with the piston to apply the force. The distal tip may have a nonslip surface for contact with the housing.

The knob is configured for rotation in one direction to increase the force applied by the set screw on the piston and in an opposition direction to decrease the force applied by the set screw on the piston, where increasing the frictional engagement locks the piston and the housing in a desired position and decreasing the frictional engagement unlocks the piston and the housing and allows repositioning of the piston and the housing relative to each other.

BRIEF DESCRIPTION OF THE DRAWINGS

These and other features and advantages of the present invention will be better understood by reference to the following detailed description when considered in conjunction with the accompanying drawings wherein.

DETAILED DESCRIPTION OF THE INVENTION

Figure 1:
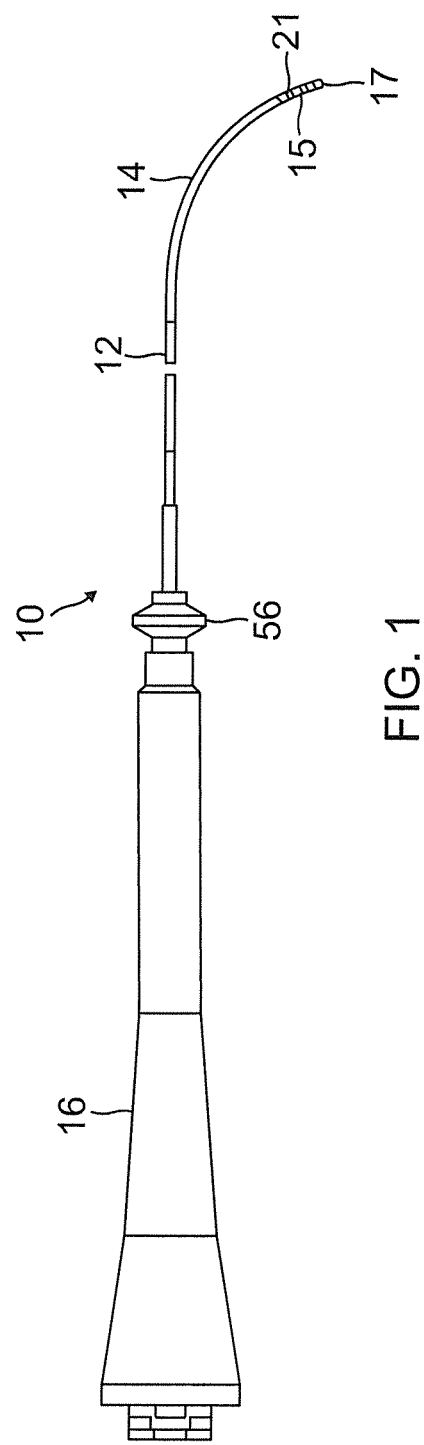
FIG. 1 is a perspective view of a catheter in accordance with an embodiment of the present invention.

FIG. 1 illustrates an embodiment of a catheter 10 with an elongated catheter body 12, an deflectable intermediate section 14, a distal section 15 with a tip electrode 17 and an improved control handle 16 employing a piston 54 housed in a handle housing for unidirectional deflection that advantageously provides a tension adjusting mechanism 55 that allows an operator to releasably lock the piston in a particular position relative to the handle housing, and allow repositioning of the piston to a different position and adjusting of the amount of force needed to reposition the piston. As such, the control handle provides a user with an enhanced ability to accurately position the catheter within the patient's body.

Figure 2:
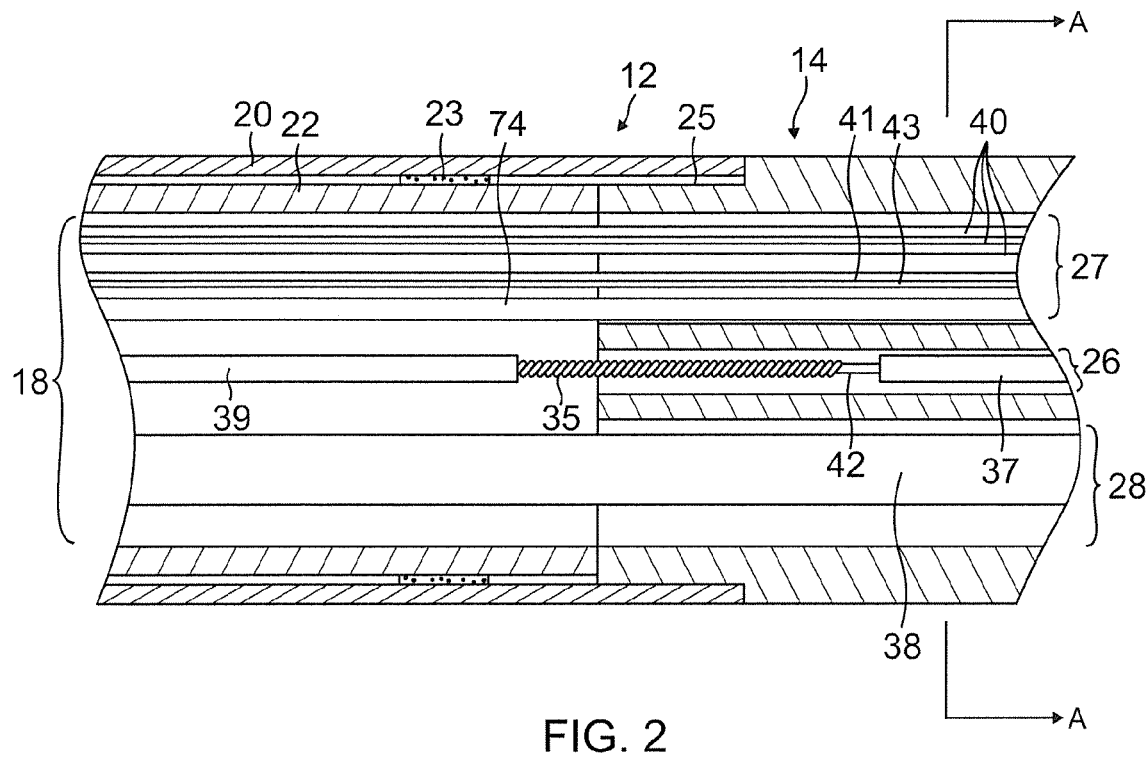
FIG. 2 is a side cross-sectional view of the catheter of FIG. 1, including a junction between a catheter body and an intermediate deflectable section.

With reference to FIGS. 1 and 2, the catheter body 12 comprises an elongated tubular construction having a single, axial or central lumen 18. The catheter body 12 is flexible, i.e., bendable, but substantially non-compressible along its length. The catheter body 12 can be of any suitable construction and made of any suitable material. A presently preferred construction comprises an outer wall 20 made of polyurethane or PEBAX. The outer wall 20 comprises an imbedded braided mesh of stainless steel or the like to increase torsional stiffness of the catheter body 12 so that, when the control handle 16 is rotated, the intermediate section 14 of the catheter 10 will rotate in a corresponding manner.

The outer diameter of the catheter body 12 is not critical, but is preferably no more than about 8 french, more preferably 7 french. Likewise the thickness of the outer wall 20 is not critical, but is thin enough so that the central lumen 18 can accommodate puller wire, lead wires, and any other desired wires, cables or tubings. If desired, the inner surface of the outer wall 20 is lined with a stiffening tube 22 to provide improved torsional stability. A disclosed embodiment, the catheter has an outer wall 20 with an outer diameter of from about 0.090 inch to about 0.94 inch and an inner diameter of from about 0.061 inch to about 0.065 inch.

Distal ends of the stiffening tube 22 and the outer wall 20 are fixedly attached near the distal end of the catheter body 12 by forming a glue joint 23 with polyurethane glue or the like. A second glue joint (not shown) is formed between proximal ends of the stiffening tube 20 and outer wall 22 using a slower drying but stronger glue, e.g., polyurethane.

Components that extend between the control handle 16 and the deflectable section 14 pass through the central lumen 18 of the catheter body 12. These components include lead wires 40 for the tip electrode 17 and ring electrodes 21 carried on the distal section 15, an irrigation tubing 38 for delivering fluid to the tip electrode, a cable 74 for an electromagnetic position/location sensor 34 carried in the distal section 15, puller wire 42 for deflecting the intermediate section 14, and a pair of thermocouple wires 41, 43 to sense temperature at the distal section 15.

Figure 2A:
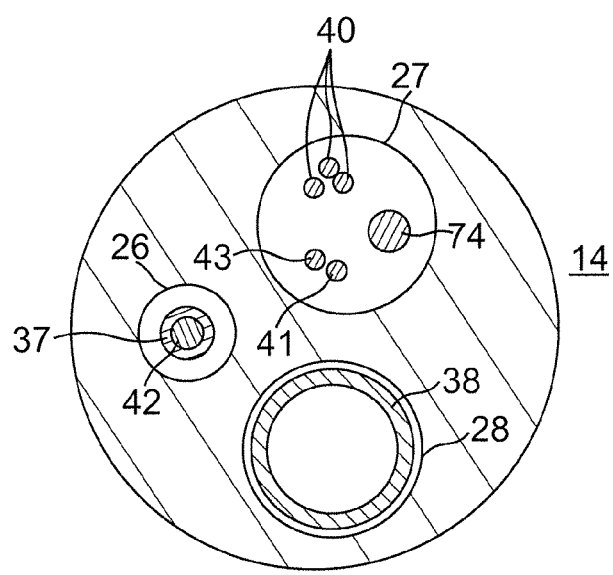
FIG. 2A is an end cross-sectional view of the intermediate deflectable section of FIG. 2, taken along line A-A.

Illustrated in FIGS. 2 and 2A is an embodiment of the intermediate section 14 which comprises a short section of tubing 19. The tubing also has a braided mesh construction but with multiple off-axis lumens, for example lumens 26, 27 and 28. The first lumen 26 carries a puller wire 42 for unidirectional deflection of the intermediate section. The second lumen 27 carries the lead wires 40, the thermocouple wires 41 and 43, and the sensor cable 74. The third lumen 28 carries the irrigation tubing 38.

The tubing 19 of the intermediate section 14 is made of a suitable non-toxic material that is more flexible than the catheter body 12. A suitable material for the tubing 19 is braided polyurethane, i.e., polyurethane with an embedded mesh of braided stainless steel or the like. The size of each lumen is not critical, but is sufficient to house the respective components extending therethrough.

A means for attaching the catheter body 12 to the intermediate section 14 is illustrated in FIGS. 2 and 2A. The proximal end of the intermediate section 14 comprises an outer circumferential notch 25 that receives an inner surface of the outer wall 20 of the catheter body 12. The intermediate section 14 and catheter body 12 are attached by glue or the like.

If desired, a spacer (not shown) can be located within the catheter body between the distal end of the stiffening tube (if provided) and the proximal end of the intermediate section. The spacer provides a transition in flexibility at the junction of the catheter body and intermediate section, which allows this junction to bend smoothly without folding or kinking. A catheter having such a spacer is described in U.S. Pat. No. 5,964,757, the disclosure of which is incorporated herein by reference.

The puller wire 42 is preferably coated with Teflon®. The puller wire can be made of any suitable metal, such as stainless steel or Nitinol and the Teflon coating imparts lubricity to the puller wire. The puller wire preferably has a diameter ranging from about 0.006 to about 0.010 inch.

The portion of the puller wire in the catheter body 12 passes through a compression coil 35 in surrounding relation thereto. The compression coil 35 extends from the proximal end of the catheter body 12 to at or near the proximal end of the intermediate section 14. The compression coil is made of any suitable metal, preferably stainless steel, and are tightly wound on itself to provide flexibility, i.e., bending, but to resist compression. The inner diameter of the compression coil is preferably slightly larger than the diameter of the puller wire. Within the catheter body 12, the outer surface of the compression coil 35 is also covered by a flexible, non-conductive sheath 39, e.g., made of polyimide tubing. The portion of the puller wires distal of the compression coil 35 may extend through a protective plastic sheath 37, e.g., of TEFLON®, to prevent the puller wire from cutting into the tubing 19 of the intermediate section 14 during deflection.

A proximal end of the puller wire 42 is anchored in the control handle 16, as described further below. A distal end of the puller wire is anchored in the distal section 15, for example, by a T-bar 44 as shown in FIG. 3.

Figure 3:
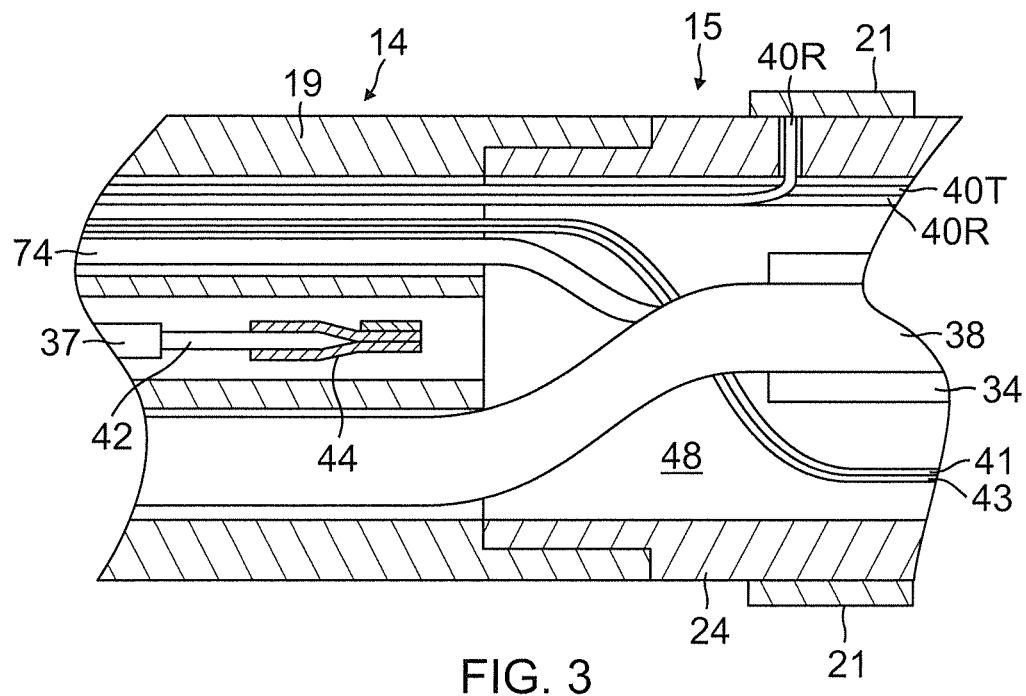
FIG. 3 is a side cross-sectional view of the catheter of FIG. 1, including a junction between the intermediate deflectable section and a distal section.
Figure 3A:
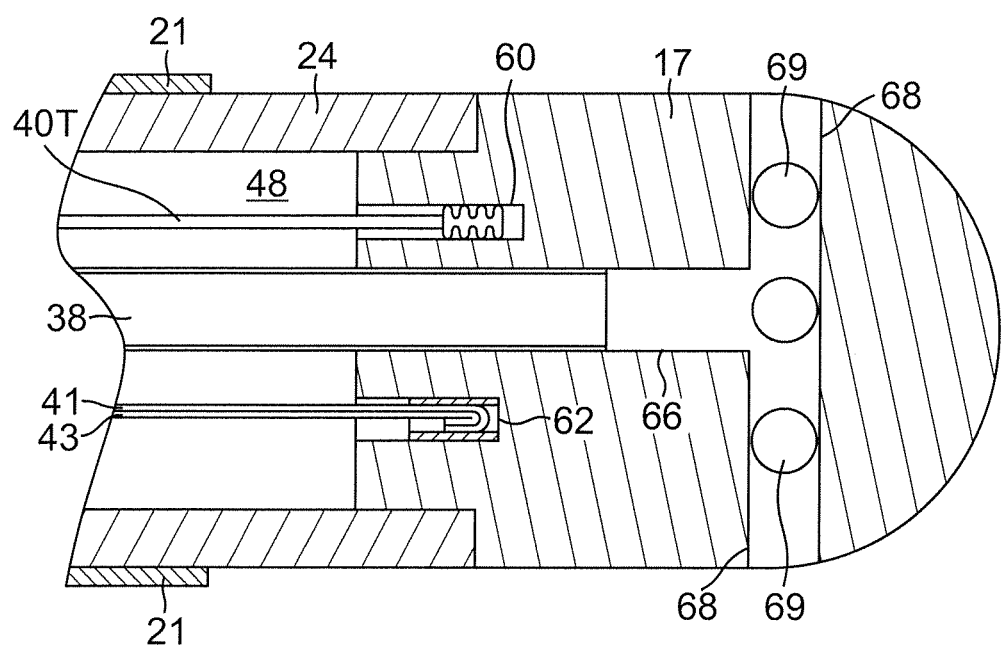
FIG. 3A is a side cross-sectional view of the catheter of FIG. 1, including a tip electrode.

As shown in FIGS. 3 and 3A, the distal section 15 comprises a tubing 24 extending between the deflectable intermediate section 14 and the tip electrode 17. The tubing 24 has a central lumen 48 which houses the sensor 34 and allows components, including the tip and ring electrode lead wires 40T and 40R, the thermocouple wire pair 41 and 43, irrigation tubing 38 and sensor cable 74, extending to the tip electrode 17 to reorient themselves. Mounted on the tubing 24 is at least one ring electrode 21.

The tip electrode 17 is received in a distal end of the tubing 24. On a proximal surface of the tip electrode, blind holes 60 and 62 are formed to receive distal ends of the tip electrode lead wire 40T and the thermocouple wires 41 and 43, respectively. Receiving a distal end of the irrigation tubing 38 is an axial passage 66 formed in the tip electrode 17. The axial passage 66 connect with transverse branches 68 and fluid ports 69 that pass fluid from the irrigation tubing to outside the tip electrode.

Figure 4:
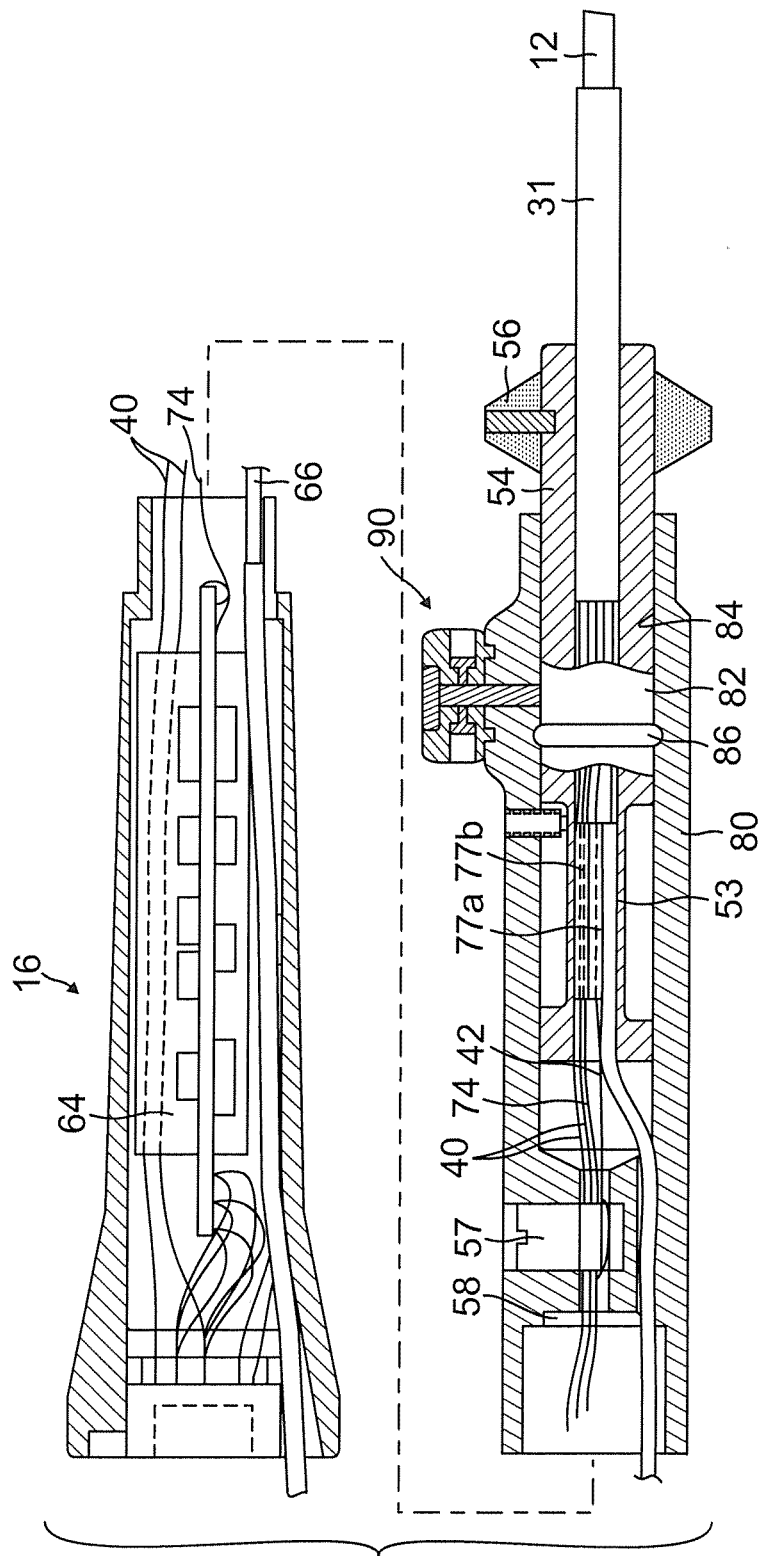
FIG. 4 is a side cross-sectional view of the catheter handle of FIG. 1.

With reference to FIG. 4, longitudinal movement of the puller wire 42 relative to the catheter body 12, which results in deflection of the tip section 12, is accomplished by suitable manipulation of the control handle 16. The distal end of the control handle 16 comprises a piston 54 that is telescopically movable relative to a control handle housing or barrel 80. An outer surface 82 of the piston is generally surrounded by and in slidable contact with an inner surface 84 of the barrel 80. The proximal end of the catheter body 12 is connected to the piston 54 by means of a shrink sleeve 31.

The piston 54 has a thumb control 56 that is distal and outside of the housing 80 and accessible to a user grasping the barrel 80 to move distally or proximally, for example, with his thumb, relative to the housing for manipulating the puller wire 42. The surfaces 82 and 84 slide against each other as the piston is moved longitudinally relative to the barrel 80 by the user via the thumb control 56. An O-ring 86 mounted on the piston and sandwiched between the surfaces 82 and 84 provides friction to provide more control and "feel" in the movement of the piston 54 relative to the barrel 80. However, in accordance with a feature of the present invention, the control handle includes a tension adjustment assembly 90 that allows the user to releasably lock the piston in place, reposition of the piston, and adjust the amount of friction between the piston and the barrel 80 in controlling the amount of force needed to move the piston 54.

Figure 5:
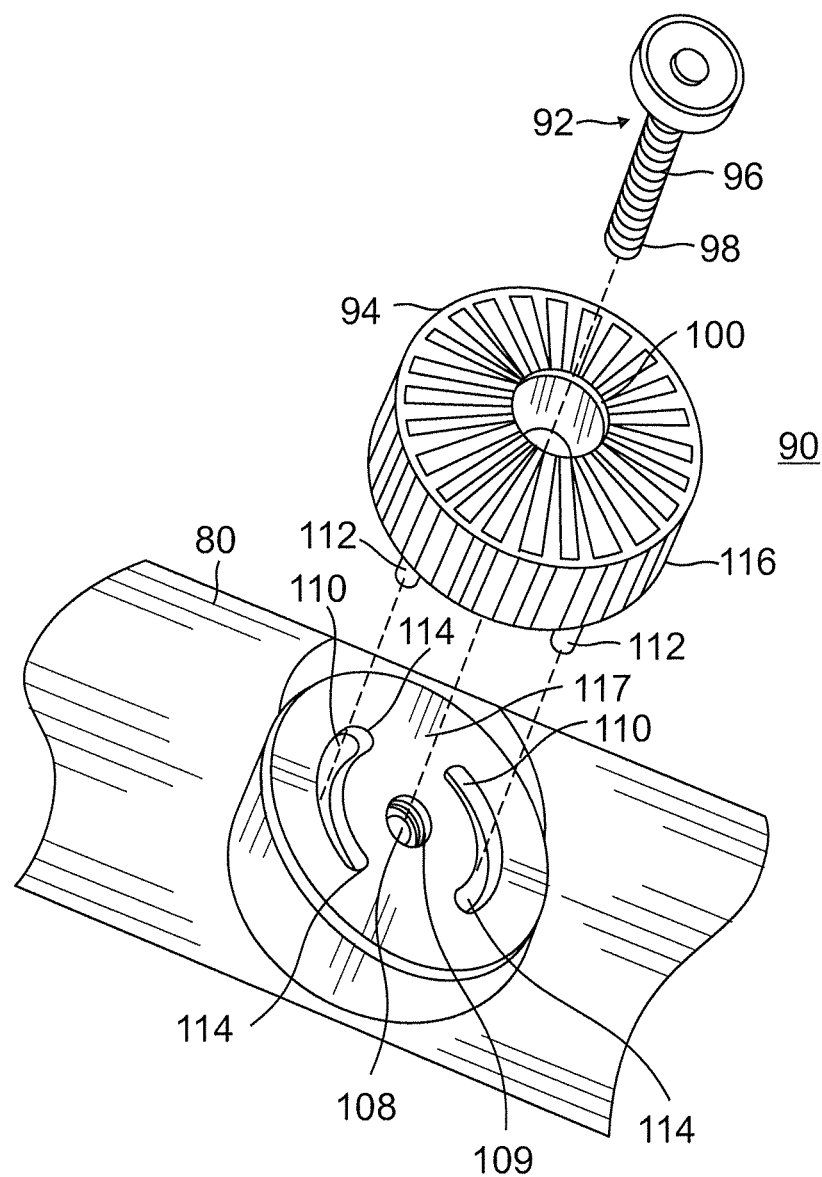
FIG. 5 is an exploded perspective view of a tension adjustment assembly in accordance with an embodiment of the present invention, including a guide plate.
Figure 6:
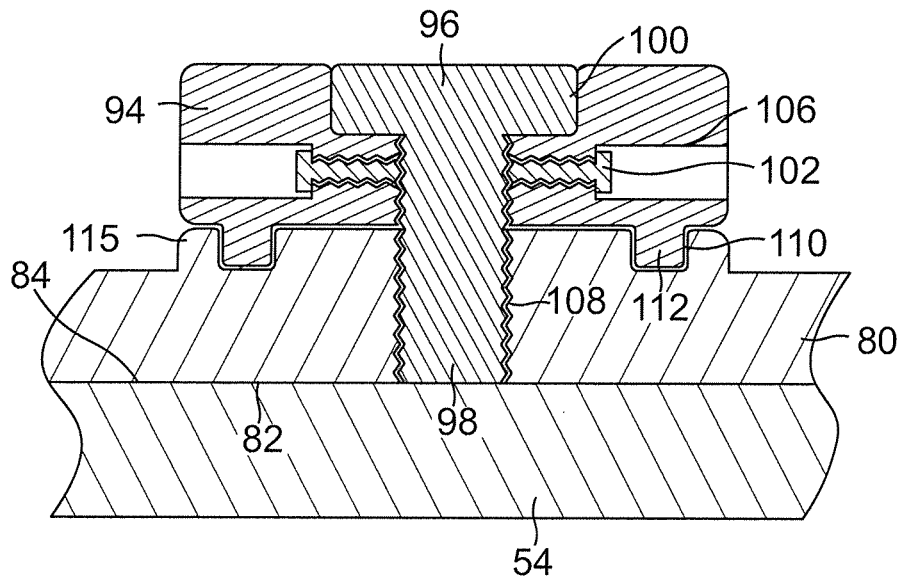
FIG. 6 is a side cross-sectional view of an tension adjustment assembly.
Figure 7:
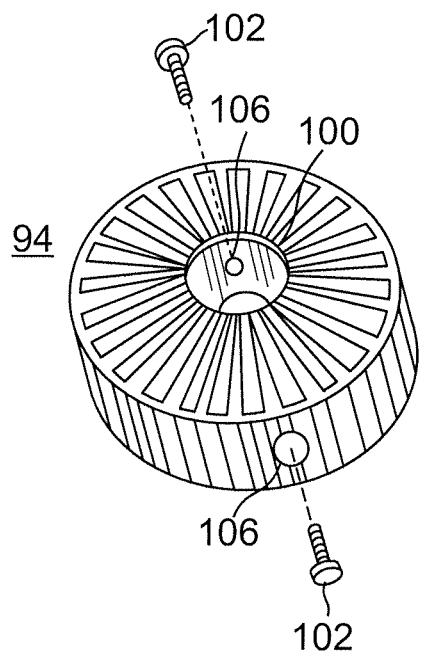
FIG. 7 is an exploded perspective view of a tension control knob of the assembly of FIGS. 5 and 6.

With reference to FIGS. 5 and 6, the tension adjustment assembly 90 includes a force or contact member 92 adapted for contact with the piston 54 and an adjustable micro-tension control knob 94 configured to adjust the amount of contact, pressure and/or friction (used interchangeably herein) exerted by the contacting member on the piston. In the illustrated embodiment, the knob has a circular cross section and the member 92 includes a set screw 96 with a nonslip, friction-inducing tip 98, e.g., of low durometer plastic, that is received in a center axial bore 100 of the knob 94. The screw 96 and the knob 94 are rotationally coupled to each other, for example, by coupling pins 102 (FIG. 7) that contact and fixedly engage the body of the screw 96 through threaded radial bores 106 formed in the knob 94. The screw and knob may also be rotationally coupled by glue or sonic welding. The distal tip 98 of the screw is received in a threaded bore 108 formed in a raised surface region 115 of the barrel 80.

Generally surrounding the bore 108 is at least one rotational travel path guide 110. In the illustrated embodiment, there are a pair of diametrically opposing, recessed semi-circular tracks. Sliding in the guides 110 are diametrically opposing projections or pins 112 extending from an inner adjacent surface of the knob 94. The guides may be formed in the raised region 115 of the barrel 80 (FIG. 6). Alternatively, the assembly 90 may include a circular guide plate 117 (FIG. 5) with the guides 110 formed thereon and a center threaded bore 109 aligned with the bore 108. The guide plate is affixed to the outer surface 82 of the barrel 80 and sandwiched between the barrel 80 and the knob 94.

In use, the user manipulates the thumb control 56 by moving it distally or proximally relative to the barrel 80 to achieve the desired deflection in the catheter. To lock, release and/or allow for more "feel" or greater tension in movability and adjustability of the thumb control 56 and the piston 54, the user can vary the tension by rotating the knob 94. By rotating the knob 94, the set screw 96 rotationally coupled thereto is either advanced into or withdrawn out of the bore 108 in the barrel for applying greater or lesser contact, pressure and/or friction forces by its distal tip 98 onto the outer surface of the barrel 80. By loosening the knob 94, movement of the piston 54 relative to the barrel 80 is increased. By tightening the knob 94, movement of the piston 54 relative to the barrel is decreased. Maximum and minimum levels of the forces are advantageously limited by ends 114 of guides 100 which prevent the pins 112 and hence the knob 94 from being rotated in either the clockwise or counterclockwise direction beyond positions that would damage the piston or allow disassembly of the assembly 90. In the illustrated embodiment, each guide 110 spans about 160 degrees. In reaching a maximum tightness as limited by the guides 110, the piston is locked in place to maintain a desired deflection. In reaching a maximum looseness as limited by the guides 110, the piston is easily movable without the set screw 96 or the knob 94 disengaging entirely from the barrel 80. Outer circumferential surface 116 of the knob may be ribbed or otherwise textured for providing a more tactile surface for the user.

In the illustrated embodiment, the tension adjustment assembly 90 is positioned closer to the distal end of the barrel 80. However, it is understood that the assembly 90 may be positioned anywhere on the barrel 80 so long as the contact member 92 or set screw 96 is able to come in and out of contact with the outer surface 82 of the barrel.

As show in FIG. 4, the puller wire 42, the lead wires 40 for the tip electrode 17 and any ring electrodes, and the electromagnetic sensor cable 74 extend through the piston 54. The puller wire 42 is anchored to an anchor pin 57 located proximal to the piston 54. The lead wires 40 and electromagnetic sensor cable 74 extend through a first tunnel 58, located near the side of the control handle 16. The electromagnetic sensor cable 74 connects to the circuit board 64 in the proximal end of the control handle. Wires 73 connect the circuit board 64 to a computer and imaging monitor (not shown).

Within the piston 54, the electromagnetic sensor cable 74 and lead wires 40 are situated within a transfer tube 77a, and the puller wire 42 is situated within another transfer tube 77b to allow longitudinal movement of the wires and cable near the glue joint 53.

The lead wires 40 pass through the lumen 28 (FIGS. 2 and 2A) of the tubing 19 of the deflectable intermediate section 14 and the central lumen 18 of the catheter body 12. The portion of the lead wires extending through the central lumen 18 of the catheter body 12, and proximal end of the lumen 27 may be enclosed within a protective sheath (not shown), which can be made of any suitable material, preferably polyimide. The protective sheath is anchored at its distal end to the proximal end of the intermediate section 14 by gluing it in the lumen 27 with polyurethane glue or the like. Each electrode lead wire has its proximal end terminating in a connector at the proximal end of the control handle 16.

The preceding description has been presented with reference to certain exemplary embodiments of the invention. Workers skilled in the art and technology to which this invention pertains will appreciate that alterations and changes to the described structure may be practiced without meaningfully departing from the principal, spirit and scope of this invention. It is understood that the drawings are not necessarily to scale. Accordingly, the foregoing description should not be read as pertaining only to the precise structures described and illustrated in the accompanying drawings. Rather, it should be read as consistent with and as support for the following claims which are to have their fullest and fairest scope.

What is claimed is:

1. A catheter, comprising:
    a flexible tubing; and
    a control handle proximal of the flexible tubing, the control handle having:
        a barrel housing and a piston in a telescopic configuration, the piston having a thumb control, the piston configured for longitudinal movement relative to the housing by a user via the thumb control for deflecting the tubing; and
        a tension adjustment assembly including:
            a force member adapted for applying a force on the piston;

a knob rotationally coupled to the force member, the knob adapted for rotation by the user to adjust the force applied on the piston by the force member; and at least one rotational guide provided on the barrel housing, the knob having at least one pin engaging the at least one rotational guide, the at least one rotational guide being configured to limit rotation of the knob, wherein the barrel housing has a bore receiving a distal portion of the force member and the at least one rotational guide extends partially around the bore.

2. The catheter of claim 1, wherein the force member includes a set screw.

3. The catheter of claim 2, wherein the set screw extends through an axial bore formed in the knob.

4. The catheter of claim 2, wherein a distal end of the set screw extends through a threaded bore formed in the barrel housing, the distal end being in adjustable contact with the piston.

5. The catheter of claim 2, wherein the set screw has a nonslip distal tip for contact with the barrel housing.

6. The catheter of claim 1, further comprising a puller wire extending through the catheter and having a proximal end anchored in the control handle, the puller wire being responsive to longitudinal movement of the piston relative to the barrel housing.

7. The catheter of claim 1, wherein the at least one rotational guide is recessed to receive at least a distal portion of the at least one pin extending from the knob.

8. The catheter of claim 1, wherein the at least one rotational guide has a generally semi-circular shape.

9. A catheter, comprising:
a flexible tubing;
a control handle proximal of the flexible tubing, the control handle having:
a barrel housing and a piston in telescopic arrangement with the barrel housing, the piston portion having a thumb control, the piston configured for longitudinal movement relative to the housing by a user via the thumb control for deflecting the tubing; and
a tension adjustment assembly including:
a set screw adapted to apply a force on the piston;
a knob mounted on the barrel housing and having an axial bore receiving a portion of the set screw, the knob and the set screw being rotationally coupled to each other; and
at least one rotational guide provided on the barrel housing, the knob having at least one pin engaging the at least one rotational guide, the at least one rotational guide being configured to limit rotation of the knob,
wherein the barrel housing has a radial bore extending between the knob and the barrel housing and the radial bore receives another portion of the set screw, and the at least one rotational guide extends partially around the radial bore, and
wherein the knob is adapted for rotation by the user to adjust the force applied by the set screw on the piston.

10. The catheter of claim 9, wherein the force includes at least one selected from the group consisting of contact, pressure and friction.

11. The catheter of claim 9, wherein a distal end of the set screw is adapted for adjustable contact with the barrel housing.

12. The catheter of claim 9, wherein the knob is configured for rotation in one direction to increase the force applied by the set screw on the piston and in an opposite direction to decrease the force applied by the set screw on the piston.

13. The catheter of claim 9, further comprising a puller wire extending through the flexible tubing, the puller wire having a proximal end anchored in the control handle.

14. A catheter, comprising:
an elongated catheter body;
an intermediate deflectable section;
a control handle proximal of the catheter body, the control handle having:
a barrel housing and a piston having a proximal portion generally surrounded by the barrel housing and a distal portion outside the barrel housing, the distal portion having a thumb control, the piston configured for longitudinal movement relative to the housing by a user via the thumb control for deflecting the intermediate section; and
a tension adjustment assembly including:
a set screw adapted to apply a force on the piston, the set screw having a head portion and a body portion;
a knob mounted on the barrel housing and having an axial bore receiving the head portion of the set screw, the knob and the set screw being rotationally coupled to each other; and
at least one rotational guide provided on the barrel housing, the knob having at least one pin engaging the at least one rotational guide, the at least one rotational guide being configured to limit rotation of the knob,
wherein the barrel housing has a radial bore extending between the knob and the barrel housing, the radial bore receives the body portion of the set screw, and the at least one rotational guide extends partially around the radial bore, and
wherein the knob is adapted for rotation by the user to adjust the force applied by the set screw on the piston.

15. A catheter, comprising:
an elongated catheter body;
an intermediate deflectable section; and
a control handle proximal of the catheter body, the control handle having:
a housing and a piston, the piston having a thumb control, the housing and the piston configured for longitudinal movement relative to each other by a user via the thumb control for deflecting the intermediate section;
an adjustment assembly including:
a set screw configured for a frictional engagement with the piston;
a knob mounted on the housing and rotatably coupled to the set screw, the knob being rotatable in one direction to increase the frictional engagement and rotatable in an opposite direction to decrease the frictional engagement; and
at least one rotational guide provided on the housing, the knob having at least one pin engaging the at least one rotational guide, the at least one rotational guide being configured to limit rotation of the knob,
wherein the housing has a bore receiving a distal portion of the set screw and the at least one rotational guide extends partially around the bore,
wherein increasing the frictional engagement locks the piston and the housing in a desired position and decreasing the frictional engagement unlocks the piston and the housing and allows repositioning of the piston and the housing relative to each other.

\* \* \* \* \*